(12) United States Patent
Ronen et al.

(10) Patent No.: US 8,201,461 B2
(45) Date of Patent: *Jun. 19, 2012

(54) APPARATUS FOR MEASURING VOLUMETRIC OR MASS FLUID FLOW

(75) Inventors: Aviram Ronen, Kiryat Motzkin (IL); Yechiel Weinstein, Atzmon (IL)

(73) Assignee: A.L. Hadas Technologies, Ltd., Ashrat (IL)

(*) Notice: Subject to any disclaimer, the term of this patent is extended or adjusted under 35 U.S.C. 154(b) by 510 days.

This patent is subject to a terminal disclaimer.

(21) Appl. No.: 11/993,601

(22) PCT Filed: Jun. 20, 2006

(86) PCT No.: PCT/IL2006/000709
§ 371 (c)(1), (2), (4) Date: Jan. 5, 2010

(87) PCT Pub. No.: WO2006/137058
PCT Pub. Date: Dec. 28, 2006

(65) Prior Publication Data
US 2010/0154508 A1 Jun. 24, 2010

Related U.S. Application Data

(60) Provisional application No. 60/693,387, filed on Jun. 22, 2005.

(51) Int. Cl.
*G01F 13/00* (2006.01)
(52) U.S. Cl. .................................................. 73/861.41
(58) Field of Classification Search ............... 73/861.41, 73/1.79, 861.71, 861.05
See application file for complete search history.

(56) References Cited

OTHER PUBLICATIONS

U.S. Appl. No. 11/273,226 Ronen et al , Apr. 12, 2006.*

* cited by examiner

*Primary Examiner* — Jewel V Thompson
(74) *Attorney, Agent, or Firm* — William H. Dippert; Eckert Seamans Cherin & Mellott, LLC

(57) ABSTRACT

Apparatus and method are provided for accurately measuring the volumetric or mass fluid flow, especially when fluid flows in a non-continuous manner using a float. A preferred embodiment comprises a tube for accumulating liquid that is periodically drained and a float confirmed within the tube that floats on the accumulating liquid. The float has magnetic properties that can be sensed so as to measure the position of the float in the tube. A controller controls a valve provided in the bottom of the tube and opens the valve so as to allow drainage of the accumulated liquid according to the positioning of the float within the tube. The valve is opened when the position of the float is in a predetermined position within the tube so that the mass or volume of the drained liquid is known.

12 Claims, 5 Drawing Sheets

APPARATUS FOR MEASURING VOLUMETRIC OR MASS FLUID FLOW

CROSS-REFERENCE TO RELATED APPLICATION

This present application claims the benefit of earlier U.S. provisional patent application Ser. No. 60/693,387, filed Jun. 22, 2005, by Ronen and Weinstein, entitled "Apparatus for Measuring Volumetric Fluid Flow".

FIELD OF THE INVENTION

The present invention relates to fluid flow measuring systems. More particularly, the present invention relates to apparatus for measuring the volumetric or mass fluid flow, especially when fluid flows in a non-continuous manner, and a method of using the same.

BACKGROUND OF THE INVENTION

Fluid management is important in many fields such as in domestic fields, scientific fields, plants and in the medical field. In the medical field, in particular, the accuracy of fluid flow measurements and fluid management can be essential. There are many methods and devices for measuring fluid flow when the flow is a continuous flow; however in the non-continuous flow regime such as drops, lack of accurate measurement techniques is prominent.

Usually, volumetric drops flow or other non-continuous flow of fluids is measured using collecting means or optical counters (for drops). An example for an optical counter is disclosed in U.S. Pat. No. 4,314,484 "Self-Compensating Optical drop Count Apparatus for Measuring Volumetric Fluid Flow" by Bowman and filed in 1979. The patent discloses a self-compensating optical drop count apparatus for measuring volumetric fluid flow by optically counting the number of drops that pass through a drop chamber. Optical counting circuitry is designed to count each drop only once. Another counter is disclosed in U.S. Pat. No. 6,640,649 "Droplet Counter for Low Flow Rates" by Paz et al. This low flow metering device for measuring the flow of an amount of fluid exceeding 0.05 ml, in which a first chamber has an inlet and an outlet in fluid communication with a second chamber, the first chamber containing an element creating laminar flow. An electronic system is positioned in the second chamber below a drop generator for counting the passage of each droplet existing therefrom, and an information processing unit is connected to the electronic system for receiving and recording information.

These means as well as other means for fluid management bear inherent mass errors that accumulatively may generate massive mistakes in the result of the measurement. Such systems for fluid management in which non-continuous measurements are performed are used in many disciplines such as scientific fields or medical fields as mentioned herein above, in which mistakes may have serious and hazardous outcomes.

The inventors of the present invention disclosed an invention that overcomes the disadvantages of existing patents and devices in this field. The invention is disclosed in PCT/IL2004/000407 published as WO/2004/101121 and describes an efficient and accurate apparatus for measuring volumetric or mass flow of fluid. However, an uncomplicated and cost effective apparatus is still needed in the art.

SUMMARY OF THE INVENTION

It is an object of the present invention to provide an apparatus and a method for accurately measuring the volumetric or mass fluid flow, especially when fluid flows in a non-continuous manner such as drops using a float.

It is another object of the present invention to provide an apparatus and a method for reliably measuring the volumetric or mass fluid flow in medical and fluid management applications such as urine measuring devices, fluid infusion or blood transfusion devices.

It is yet another object of the present invention to provide an apparatus and method for measuring the volumetric or mass fluid flow without counting the drops so as to eliminate inherent errors generated from counting individual drops.

And another object of the present invention is to provide an apparatus and method for measuring the volumetric or mass fluid flow that is simple to manufacture and is cost effective.

Therefore, it is provided in accordance with a preferred embodiment of the present invention an apparatus for measuring mass flow of fluid, said apparatus comprising:

a tube having an upper end adapted to receive the fluid and a bottom end through which the fluid is adapted to drain;

a float confined within said tube adapted to float on liquid that can accumulate within said tube, wherein said float has magnetic properties;

a measuring means adapted to measure the position of said float by sensing said magnetic properties;

a valve provided in said bottom end wherein said valve is adapted to open so as to allow drainage of the liquid accumulated within said tube;

a controller adapted to control said valve;

whereby said valve is opened when said measuring means measures the position of the float to be in a predetermined position within said tube.

Furthermore and in accordance with another preferred embodiment of the present invention, said measuring means is a differential transformer.

Furthermore and in accordance with another preferred embodiment of the present invention, the fluid is dripping in drops to said tube from said upper end.

Furthermore and in accordance with another preferred embodiment of the present invention, the fluid flows in a continuous manner to said tube.

Furthermore and in accordance with another preferred embodiment to the present invention, the apparatus further comprising a calibrating means adapted to allow calibrating the position of said float within said tube.

Furthermore and in accordance with another preferred embodiment of the present invention, said calibrating means is a DC coil.

Furthermore and in accordance with another preferred embodiment of the present invention, said DC coil is a solenoid.

It is also provided in accordance with another preferred embodiment of the present invention, a method for measuring the volumetric flow of fluid comprising:

providing a tube having an upper end and a bottom end;

providing a float having magnetic properties wherein said float is confined within said tube and is adapted to move freely within said tube;

providing a magnetic means adjacent to said tube, wherein said magnetic means is adapted to measure the position of said float within said tube;

providing a valve in said bottom end;

providing a controller adapted to control said valve;

allowing the fluid to accumulate within said tube;

measuring the position of said float within said tube;

ordering said valve to open using said controller when said magnetic means indicates the float reached a predetermined position;

allowing drainage of the liquid;

Whereby the volumetric flow rate can be calculated from the number of times said valve opened in a predetermined time.

Furthermore and in accordance with another preferred embodiment of the present invention, said method further comprises self-calibrating the position of said float within said tube by a magnetic means that is adapted to exert force on said float.

Furthermore and in accordance with another preferred embodiment of the present invention, said magnetic means is a DC coil.

Furthermore and in accordance with another preferred embodiment of the present invention, said DC coil is a solenoid.

Additionally and in accordance with another preferred embodiment of the present invention, said controller is provided with a calibration curve that allows self calibrating the position of said float.

BRIEF DESCRIPTION OF THE FIGURES

In order to better understand the present invention and appreciate its practical applications, the following Figures are attached and referenced herein. Like components are denoted by like reference numerals.

It should be noted that the figures are given as examples and preferred embodiments only and in no way limit the scope of the present invention as defined in the appending Description and Claims.

DETAILED DESCRIPTION OF THE INVENTION

In fluid management fields, especially where the flow rates are non-continuous and establish a regime of drops, it is customary to measure the volumetric or mass flow using optical counters of drops. Those methods bear inherent errors that are originated from the size and shape of the droplets. The present invention provides a unique and novel apparatus that accumulates the drops so that characteristics of the drops themselves that outcome from various physical characters has no effect on the measurement.

Since in apparatii used today especially in medical fields, the drops are counted individually, any movement or change in character of the fluid throughout the measurement may cause an enormous mistake. The outcome of such a mistake is crucial since drug management is decided according to the results of the measurement. However, similar errors in the scientific field have also severe outcomes.

The present invention provides a new and unique apparatus for measuring volumetric or mass flow of fluid. Throughout the following text, the use of the terms volumetric flow and mass flow are used arbitrarily. The transition from fluid volume to fluid mass and vice versa is known in the art, simple, and can be incorporated in the controller software in accordance with the fluid that is being managed.

Figure 1:
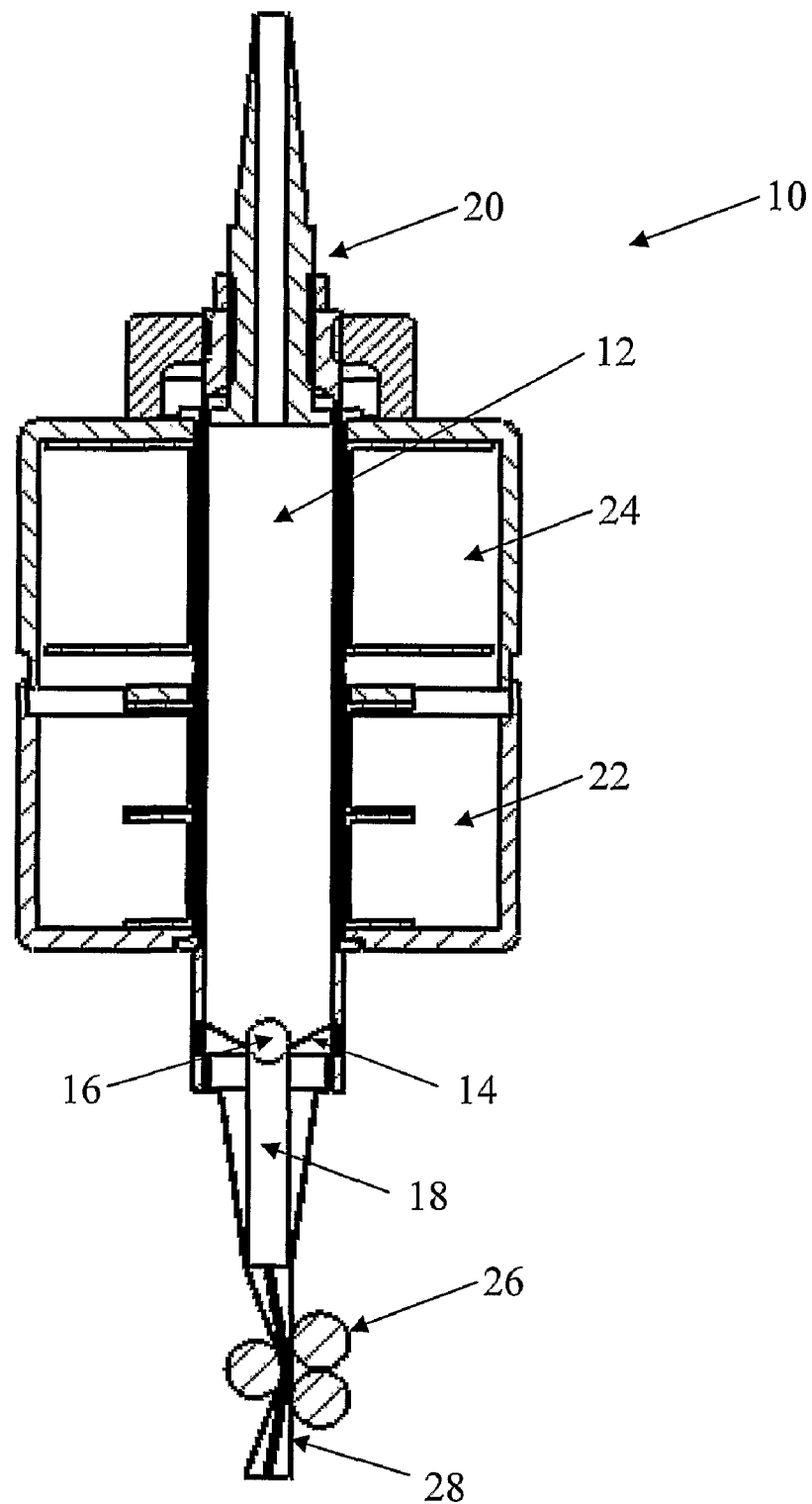
FIG. 1 illustrates a cross sectional view of an apparatus for measuring the mass flow of fluid drops in accordance with a preferred embodiment of the present invention.

Reference is now made to FIG. 1 illustrating a cross sectional view of an apparatus for measuring the volumetric flow of fluid drops in accordance with a preferred embodiment of the present invention. An apparatus for measuring a fluid volumetric flow 10 comprises a tube 12 through which fluids can pass. Tube 12 is preferably a tapered tube having a narrowing 14 at the bottom side of tube 12 extending into a conduit 18. A float 16 that is provided within tube 12 is designed so as to have a size by which float 16 is prevented from entering conduit 18. It should be noted that any other method or means preventing float 16 from falling into conduit 18 can be employed in the present invention. The upper portion of tube 12 is provided with a tapering duct 20 adapted to be connected to a tube through which liquid is received (the tube is not shown in the Figures).

Float 16 is adapted to move within tube 12 upwardly and downwardly by floating on liquid that is accumulated within. Float 16 is made of or provided with substance or elements that impart the float with magnetic properties. An AC coil 22, such as differential transformer, circumscribes tube 12 substantially adjacent to the positioning of float 16. AC coil 22 generates a magnetic field about tube 12 and is adapted to allow measurement of the accurate positioning of float 16 in any instant through an output coil.

A DC coil 24, such as a solenoid, is provided circumscribing tube 12. DC coil 24 is adapted to exert force on float 16 that comprises magnetic elements and can maintain the float in a predetermined position within tube 12. The positioning of the float in any position within tube 12 is calibrated in the following manner: the float is maintained in a predetermined position that is recorded by the output of AC coil 22. This step is being generated for any position of the float within the tube so as to establish a calibration curve so that any output of AC coil 22 is a function of a known positioning of float 16. The positioning of the float within the tube together with the diameter of the tube indicates the volume or mass of the liquid. Upon any change of the positioning of the float from the calibration curve, correction may be performed.

A valve 26 is provided in a conduit 28 that acts as a drain and is positioned as an extension of conduit 18. Valve 26 is adapted to be electrically activated and preferably in accordance with the output of float 16 positioning measured by AC coil 22. A controller (not shown in the Figures) is adapted to control the activation of the valve so as to allow drainage of the liquid.

Figure 2:
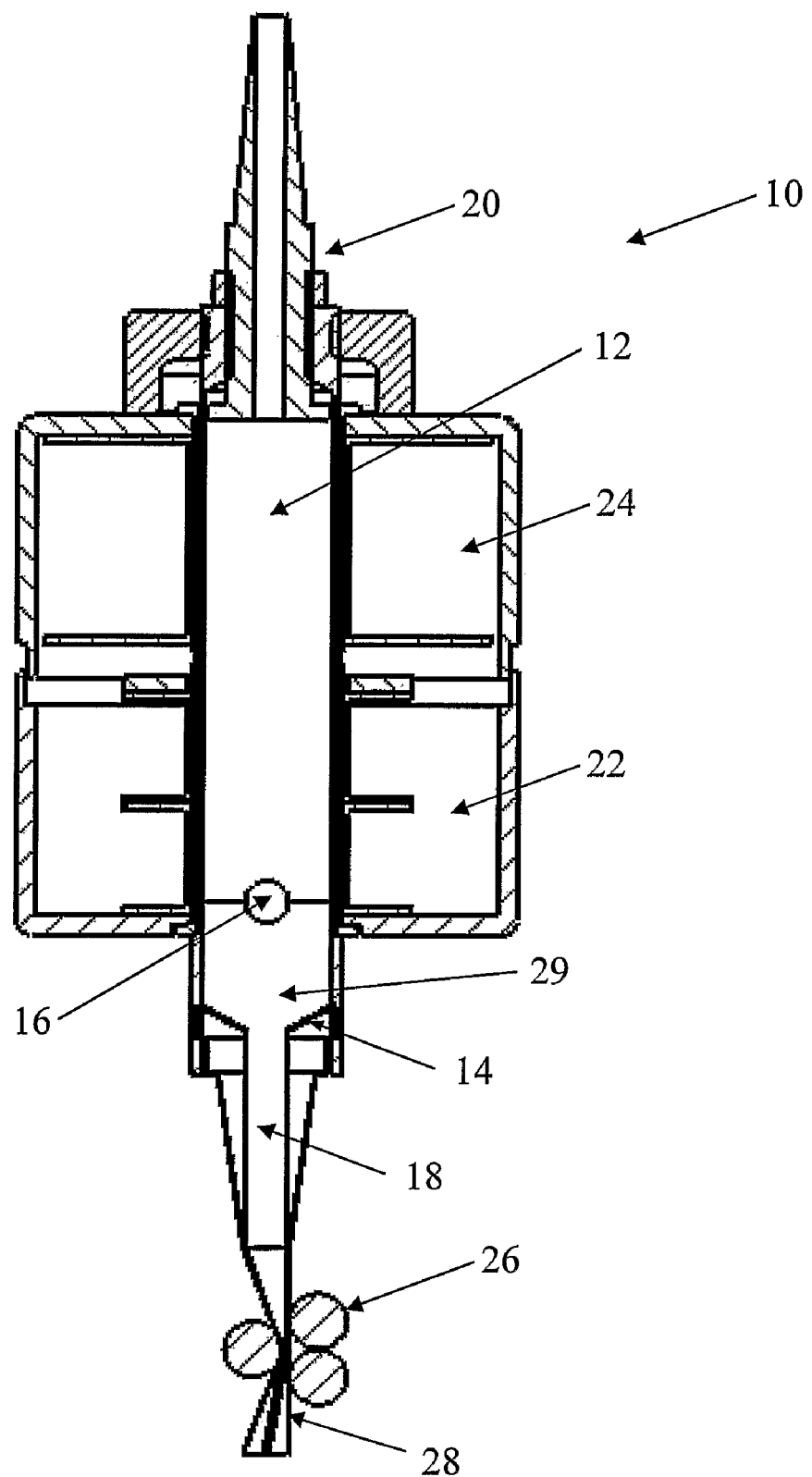
FIG. 2 illustrates a cross sectional view of the apparatus shown in FIG. 1, in accumulating state.
Figure 3:
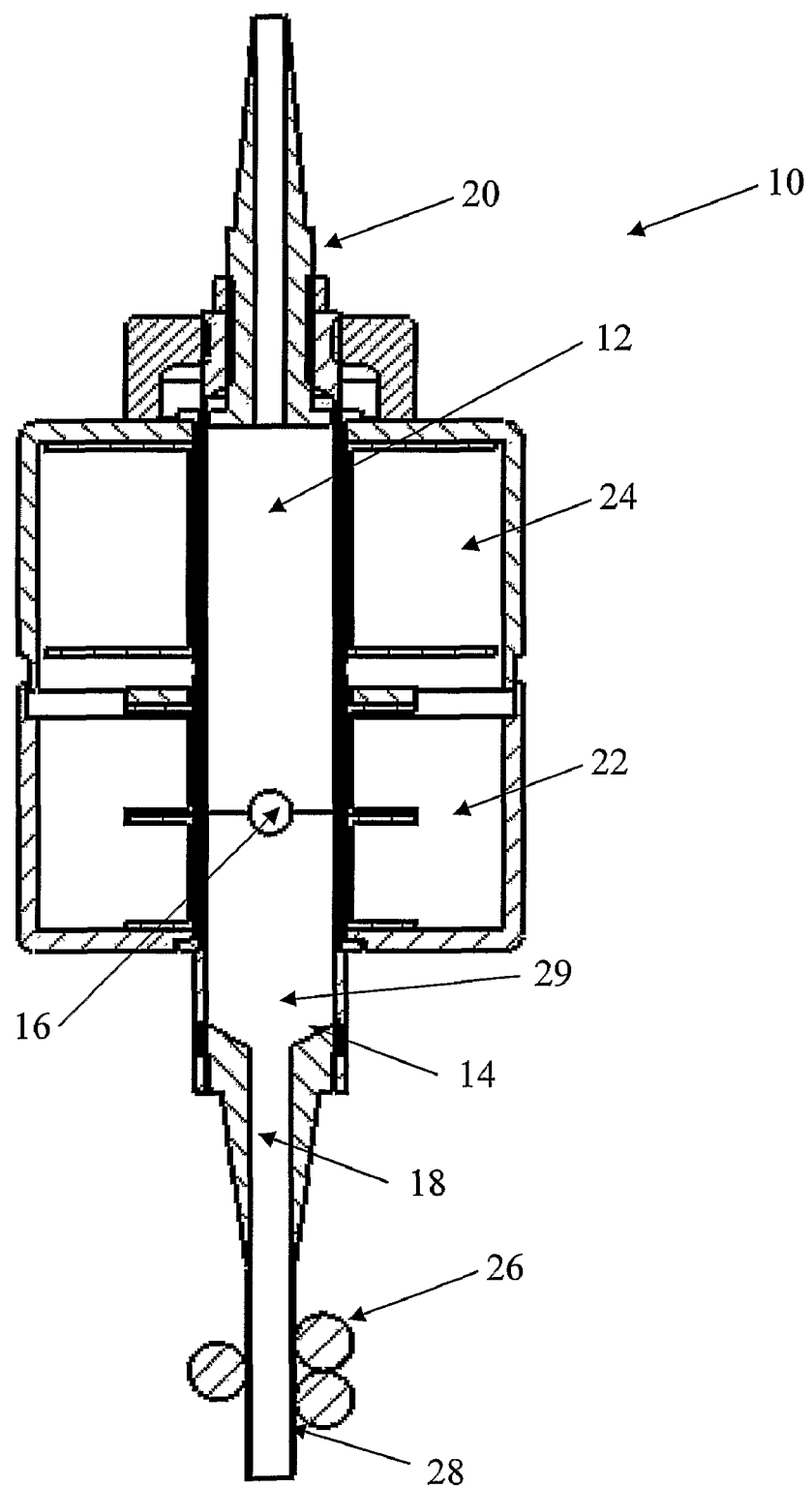
FIG. 3 illustrates a cross sectional view of the apparatus shown in FIG. 1, wherein the level of liquid is at a predetermined point for draining.

Reference is now made to FIGS. 2 and 3 illustrating a cross sectional view of the apparatus shown in FIG. 1, in accumulating state and when the level of liquid is at a predetermined point for draining. Float 16 is floating on top of liquid 28 that is accumulating within tube 12. Since valve 26 is in a closed state, the liquid that is received through tapering duct 20 is accumulated. The level of the liquid is getting higher until it reached a predetermined position. FIG. 3 illustrates a position of the liquid level that is a predetermined position before the liquid is drained through conduit 18, conduit 28 and valve 26.

According to the method of the present invention, at a predetermined value measured by output coil 22 that indicates float 16 had reached the predetermined position, valve 26 receives a command to open up.

Figure 4:
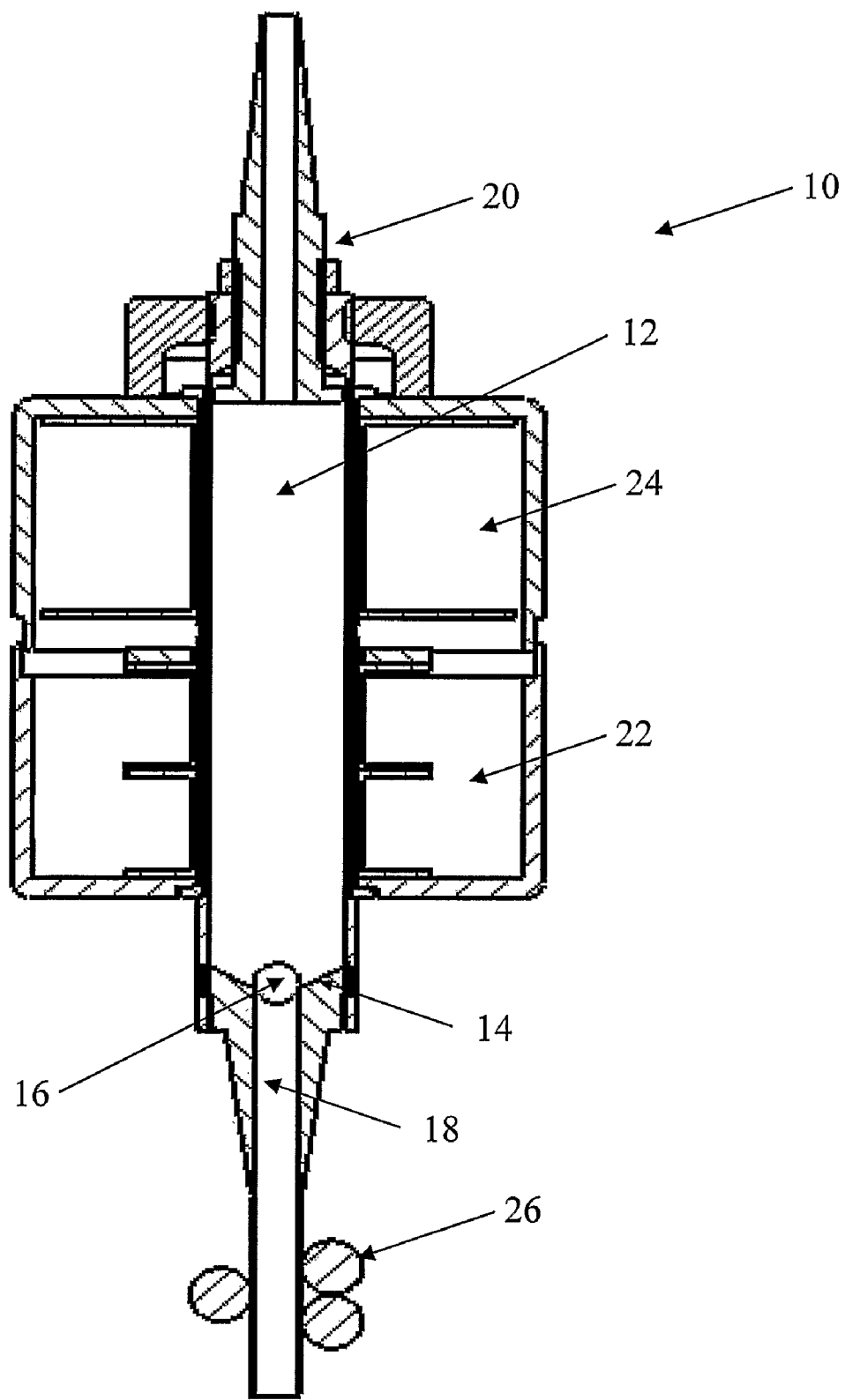
FIG. 4 illustrates a cross sectional view of the apparatus shown on FIG. 1, in draining state.

Reference is now made to FIG. 4 illustrating a cross sectional view of the apparatus shown on FIG. 1, in draining state. Valve 26 opens in accordance with the command and allows the accumulated liquid to drain. Float 16 returns to its original state, at the bottom of tube 12. One of the main advantages of the apparatus of the present invention is the ability to provide a sufficiently large draining tube that reduces the error occurs during the drainage process in which liquid continues to drip to within the tube. This amount can be estimated by parameters such as time of drainage and the rate of drops dripping before the drainage.

It should be noticed that the flow can be measured when the fluid flows in drops or in a continuous manner, and there is no limitation as for the flow rate. The fluid can be of any viscosity or density while in any case the flow rate can be measured by the apparatus and method of the present invention. The measurement is accurate if the flow regime is even markedly changed during measurements and there will be no impact of the rate on the accuracy of the measurement.

Figure 5:
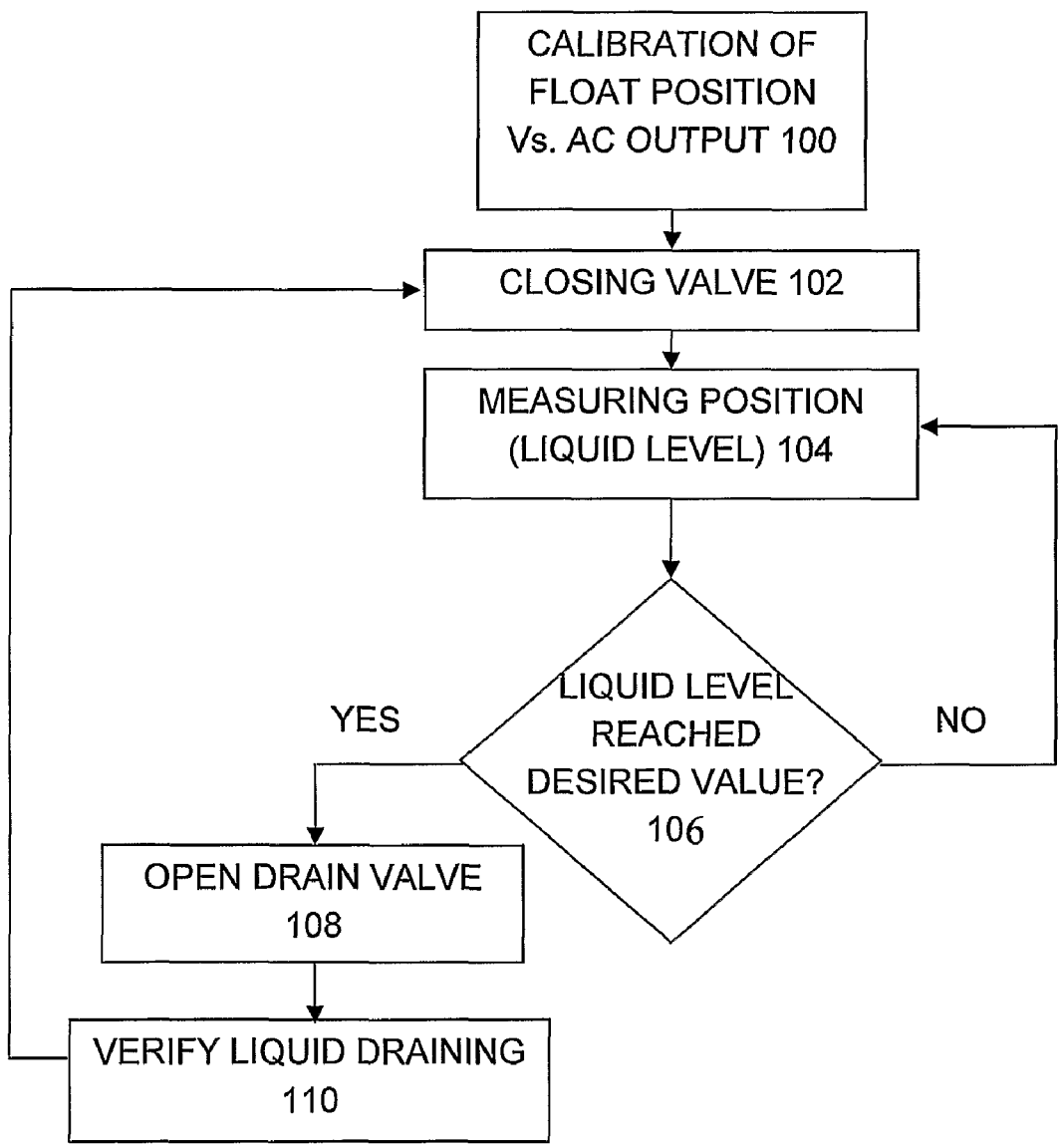
FIG. 5 illustrates a block diagram of operations made by a controller controlling an apparatus for measuring the mass flow of fluid drops in accordance with a preferred embodiment of the present invention.

Reference is now made to FIG. 5 illustrating a block diagram of operations made by a controller controlling an apparatus for measuring the mass flow of fluid drops in accordance with a preferred embodiment of the present invention. As mentioned herein before, the positioning of the float in any position within the tube is calibrated in the following manner: the float is maintained in a predetermined position that is recorded by the output of the AC coil that circulates the tube. This step is being generated for any position of the float within the tube so as to establish a calibration curve so that any output of the AC coil is a function of a known positioning of the float. The calibration curve is maintain within the controller and is being corrected in case needed 100.

The controller maintains the valve in the bottom of the tube closed 102 at any time during the collection of liquid within the tube and measures the positioning of the float in the tube 104 at all times using the calibration curve. The positioning of the float indicates the level of the liquid since the float is floating on top of the liquid. Then, the controller checks whether the positioning of the float has reached a predetermined positioning 106.

If the level of the liquid within the tube has reached a certain predetermined level, a know mass or volume of liquid is maintain within the tube and this mass is drained. The controller operates in order to open the draining valve 108 and verifies that the liquid is drained 110. The draining valve is being closed again 102 in order to allow collection of new liquid in the tube. If the liquid level has not reached the predetermined level, the positioning of the float is continued to be monitored 104.

The tube provided with the float can be a disposable part. In order to start measurements, the disposable part of the tube and the float is connected to a receiving duct that is adapted to allow passage of liquids to be measured. On the other side, the tube is connected to a drain conduit that is adapted to allow drainage of the liquid that is accumulating in the tube. Draining in accordance with the present invention is preferably performed when the float reaches a predetermined position within the tube.

It should be clear that the description of the embodiments and attached Figures set forth in this specification serves only for a better understanding of the invention, without limiting its scope as covered by the following Claims.

It should also be clear that a person skilled in the art, after reading the present specification can make adjustments or amendments to the attached Figures and above described embodiments that would still be covered by the following Claims.

The invention claimed is:

1. An apparatus for measuring volumetric flow of fluid, said apparatus comprising:
    a tube having an upper end adapted to receive the fluid and a bottom end through which the fluid is adapted to drain;
    a float confined within said tube adapted to float on liquid that can accumulate within said tube, wherein said float has magnetic properties;
    a measuring device adapted to measure the position of said float by sensing said magnetic properties;
    a valve provided in said bottom end wherein said valve is adapted to open so as to allow drainage of the liquid accumulated within said tube; and
    a controller adapted to control said valve,
    whereby said valve is opened when said measuring device measures the position of the float to be in a predetermined position within said tube.

2. The apparatus as claimed in claim 1, wherein said measuring device is a differential transformer.

3. The apparatus as claimed in claim 1, wherein the fluid is dripping in drops to said tube from said upper end.

4. The apparatus as claimed in claim 1, wherein the fluid flows in a continuous manner to said tube.

5. The apparatus as claimed in claim 1, further comprising a calibrator for calibrating the position of said float within said tube.

6. The apparatus as claimed in claim 5, wherein said calibrator ing means is a DC coil.

7. The apparatus as claimed in claim 6, wherein said DC coil is a solenoid.

8. A method for measuring the volumetric flow of fluid, comprising:
    providing a tube having an upper end and a bottom end;
    providing a float having magnetic properties wherein said float is confined within said tube and is adapted to move freely within said tube;
    providing a magnetically-based device adjacent to said tube, wherein said magnetically-based device is adapted to measure the
    position of said float within said tube;
    providing a valve in said bottom end;
    providing a controller adapted to control said valve;
    allowing the fluid to accumulate within said tube;
    measuring the position of said float within said tube;
    ordering said valve to open using said controller when said magnetically-based device indicates the float reached a predetermined position; and
    allowing drainage of the liquid,
    whereby the volumetric flow rate can be calculated from the number of times said valve opened in a predetermined time.

9. The method as claimed in claim 8, wherein said method further comprises self-calibrating the position of said float within said tube by another magnetically-based device that is adapted to exert force on said float.

10. The method as claimed in claim 9, wherein said magnetically-based device is a DC coil.

11. The method as claimed in claim 10, wherein said DC coil is a solenoid.

12. The method as claimed in claim 9, wherein said controller is provided with a calibration curve that allows self calibrating the position of said float.

* * * * *